United States Patent
Koper et al.

(10) Patent No.: US 7,863,492 B2
(45) Date of Patent: Jan. 4, 2011

(54) PRODUCTION OF LINEAR ALKYL BENZENE

(75) Inventors: Edward Ludovicus Koper, Secunda (ZA); Ivan Greager, Sundowner (ZA); Jan Hendrik Scholtz, Parkview (ZA); Johan Pieter de Wet, Vanderbijlpark (ZA); Mieke Ann Desmet, Weltevredenpark (ZA); Wilhelmina Jansen, Vanderbijlpark (ZA); Paul Jacobson, Sasolburg (ZA)

(73) Assignee: Sasol Technology (Proprietary) Limited, Rosebank (ZA)

( * ) Notice: Subject to any disclaimer, the term of this patent is extended or adjusted under 35 U.S.C. 154(b) by 1161 days.

(21) Appl. No.: 10/549,769

(22) PCT Filed: Mar. 10, 2004

(86) PCT No.: PCT/IB2004/000657

§ 371 (c)(1),
(2), (4) Date: Jul. 31, 2006

(87) PCT Pub. No.: WO2004/080929

PCT Pub. Date: Sep. 23, 2004

(65) Prior Publication Data
US 2007/0066859 A1    Mar. 22, 2007

Related U.S. Application Data

(60) Provisional application No. 60/453,419, filed on Mar. 10, 2003, provisional application No. 60/453,418, filed on Mar. 10, 2003, provisional application No. 60/496,816, filed on Aug. 21, 2003.

(30) Foreign Application Priority Data

| Mar. 10, 2003 | (ZA) | ................................ 2003/1937 |
| Mar. 10, 2003 | (ZA) | ................................ 2003/1939 |
| Aug. 21, 2003 | (ZA) | ................................ 2003/6524 |

(51) Int. Cl.
*C07C 2/68* (2006.01)
(52) U.S. Cl. ............................ 585/323; 208/49; 208/79; 208/134
(58) Field of Classification Search ................ 585/323; 210/634–643; 208/49, 78–79, 134–140
See application file for complete search history.

(56) References Cited

U.S. PATENT DOCUMENTS 3,674,885 A    7/1972    Griesinger et al.

(Continued)

FOREIGN PATENT DOCUMENTS

DE    199 11 910 A1    9/2000

(Continued)

OTHER PUBLICATIONS

Kocal et al., "Production of linear alkylbanzene," *Catalysis*, 2001 (CAS Abstract No. 136:249302).

(Continued)

*Primary Examiner*—Glenn A Caldarola
*Assistant Examiner*—Brian McCaig
(74) *Attorney, Agent, or Firm*—Brinks Hofer Gilson & Lione

(57) ABSTRACT

This invention relates to a process for producing linear alkyl benzene and linear paraffins, the process including the steps of obtaining a hydrocarbon condensate containing olefins, paraffins and oxygenates from a low temperature Fischer-Tropsch reaction; a) fractionating a desired carbon number distribution from the hydrocarbon condensate to form a fractionated hydrocarbon condensate stream; b) extracting oxygenates from the fractionated hydrocarbon condensate stream from step a) to form a stream containing olefins and paraffins; c) alkylating the stream containing olefins and paraffins from step b) with benzene in the presence of a suitable alkylation catalyst; and d) recovering linear alkyl benzene and linear paraffin.

25 Claims, 2 Drawing Sheets

U.S. PATENT DOCUMENTS

| | | | |
|---|---|---|---|
| 4,219,686 | A | 8/1980 | Petrillo et al. |
| 4,447,664 | A | 5/1984 | Murchison et al. |
| 4,513,156 | A | 4/1985 | Tabak |
| 4,603,225 | A | 7/1986 | Colaianne et al. |
| 4,686,317 | A | 8/1987 | Quann et al. |
| 5,196,624 | A | 3/1993 | Threlkel et al. |
| 5,196,625 | A | 3/1993 | Threlkel et al. |
| 6,111,158 | A | 8/2000 | Marinangeli et al. |
| 6,375,830 | B1 | 4/2002 | Clark et al. |
| 6,392,109 | B1 | 5/2002 | O'Rear et al. |
| 2002/0082182 | A1 | 6/2002 | Kott et al. |
| 2002/0115732 | A1 | 8/2002 | Moore, Jr. et al. |

FOREIGN PATENT DOCUMENTS

| | | |
|---|---|---|
| EP | 0 807 616 A2 | 11/1997 |
| EP | 1 160 309 A1 | 12/2001 |
| GB | 669313 | 4/1952 |
| GB | 990744 | 4/1965 |
| GB | 2 258 258 A | 2/1993 |
| WO | WO 90/11986 A1 | 10/1990 |
| WO | WO 99/05082 A1 | 2/1999 |
| WO | WO 99/05241 A1 | 2/1999 |
| WO | WO 99/05242 A1 | 2/1999 |
| WO | WO 00/14184 A2 | 3/2000 |
| WO | WO 01/02325 A1 | 1/2001 |
| WO | WO 01/64610 A1 | 9/2001 |
| WO | WO 02/31085 A1 | 4/2002 |
| WO | WO 02/44114 A1 | 6/2002 |

OTHER PUBLICATIONS

Marr et al., "Recent Innovations in linear alkylbenzene process technology," *World Surfactants Congress*, May 29-Jun. 2, 2000, (CAS Abstract No. 136:249396).

Sharma et al., "Synthesis of detergents from Fischer-Tropsch waxes: Part I. Synthesis of heptyl benzene sulphonate," *Research and Industry*, Sep. 20, 1975.

Sharma et al., "Synthesis of detergents from Fischer-Tropsch waxes: Part II. Synthesis of docedyl benzene sulphonate," *Indian J. Technology*, 1977 (CAS Abstract No. 89:56861).

US 7,863,492 B2

PRODUCTION OF LINEAR ALKYL BENZENE

CROSS REFERENCE TO RELATED APPLICATIONS

The present patent application is the National Stage of International Application No. PCT/IB2004/00657, filed Mar. 10, 2004, which claims the priority of South African Application No. 2003/1937, filed Mar. 10, 2003, claims the benefit under 35 U.S.C. §119(e) of U.S. Provisional Patent Application Ser. No. 60/453,419, filed Mar. 10, 2003, claims the priority of South African Application No. 2003/1939, filed Mar. 10, 2003, claims the benefit of U.S. Provisional Patent Application Ser. No. 60/453,418, filed Mar. 10, 2003, claims the priority of South African Application No. 2003/6524, filed Aug. 21, 2003, claims the benefit of U.S. Provisional Patent Application Ser. No. 60/496,816, filed Aug. 21, 2003.

BACKGROUND OF THE INVENTION

This invention relates to a process for producing linear alkyl benzene and linear paraffin.

Alkyl benzene derivatives, such as alkyl benzene sulphonates, are among others, used in detergent and surfactant product applications. Environmental legislation requires that these products are biodegradable. It is well known that, to be biodegradable, it is important for the alkyl chain to be linear, i.e. with very little or no branching and low, if any, quaternary carbons.

In conventional processes for producing linear alkyl benzenes, a hydrocarbon stream is hydrogenated in order to remove contaminants such as sulphur, nitrogen and oxygen contaminants that may be present. Hydrogenation also converts olefin species in the stream to paraffins. Following the hydrogenation reaction, the resulting paraffin stream is fractionated into various carbon ranges. A carbon range, for example the $C_8$ to $C_{16}$ range, which includes branched paraffins, is passed through a molecular sieve. The branched paraffins are rejected as a raffinate stream, whilst the linear paraffins are passed through a dehydrogenation reactor to form an olefin/paraffin mixture. This mixture is then fed to an alkylation plant and reacted with benzene to form linear alkyl benzene (LAB), with recycling of unreacted paraffins to the dehydrogenation reactor. The linear alkyl benzene is then sulphonated to form linear alkyl benzene sulphonates (LAS). A problem with this approach is the relatively high cost of paraffinic starting material and the high cost associated with the production of linear paraffins from kerosene feedstocks.

United Kingdom Patent No. 669,313 in the name of California Research Corporation discloses the use of a hydrocarbon condensate from the Fischer-Tropsch process as a feedstock in the production of alkyl benzene. This reference is limited to the use of "high temperature" Fischer-Tropsch processes wherein the Fischer-Tropsch reaction is carried out at temperatures of approximately 300° C. and higher, for the production of the hydrocarbon condensate. The high temperature Fischer-Tropsch processes were found to be suitable because the hydrocarbon condensate contains a high concentration of olefins; usually in the region of around 70%. The preferred catalysts in the Fischer-Tropsch process for the production of the hydrocarbon condensate in this reference are iron-containing catalysts. This reference states that Fischer Tropsch feedstock produced results in poor quality Linear Alkyl Benzene due to odour and wetting problems caused by carbonyl i.e. oxygenate content of the Fischer-Tropsch feedstock. The preferred method for addressing this problem is by adsorption of carbonyl compounds from the Fischer-Tropsch feedstock using activated carbon and silica gel in a guard bed. This process is only feasible for feeds with low oxygenate concentrations. Also, in the example in this reference the olefin recovery is less than 25%, i.e. the olefin content is not preserved.

U.S. Pat. No. 3,674,885 in the name of Atlantic Richfield Company aims to show that a paraffin/olefin mixture obtained from a Fischer-Tropsch reactor can be alkylated together with chlorinated paraffins by operating the alkylation at elevated temperatures. Fresh Fischer-Tropsch feed is mixed with chlorinated paraffin and charged to the alkylation reactor, the unreacted paraffin is separated and partially activated by chlorination and then mixed with fresh Fischer-Tropsch based feedstock before alkylation. A synthetic mixture of dodecane and dodecene is used in the examples to represent Fischer-Tropsch feedstock. This reference does not acknowledge the difficulties faced when attempting to use Fischer-Tropsch feedstock for alkylation and is not considered to be relevant to the present invention.

SUMMARY OF THE INVENTION

According to the invention there is provided a process for producing linear alkyl benzene and linear paraffins, the process including the steps of obtaining a hydrocarbon condensate containing olefins, paraffins and oxygenates from a low temperature Fischer-Tropsch reaction;
    a) fractionating a desired carbon number distribution from the hydrocarbon condensate to form a fractionated hydrocarbon condensate stream;
    b) extracting oxygenates from the fractionated hydrocarbon condensate stream from step a) to form a stream containing olefins and paraffins;
    c) alkylating the stream containing olefins and paraffins from step b) with benzene in the presence of a suitable alkylation catalyst; and
    d) recovering linear alkyl benzene and linear paraffin.

Typically, the low temperature Fischer-Tropsch reaction is carried out at a temperature of 160° C.-280° C., preferably 210° C.-260° C., and a Fischer-Tropsch catalyst, preferably in the presence of a cobalt catalyst to provide a hydrocarbon condensate containing 60 to 80% by weight paraffins and 10 to 30% by weight, typically less than 25% by weight, olefins. The olefins so produced have a high degree of linearity of greater than 92%, typically greater than 95%. The paraffins so produced have a degree of linearity of greater than 92%.

The hydrocarbon condensate, in step a), is fractionated into the $C_8$ to $C_{16}$ range, preferably into the $C_{10}$ to $C_{13}$ range.

The oxygenates may be extracted, in step b), by distillation, liquid-liquid extraction or dehydration, preferably liquid-liquid extraction. A light solvent such as a mixture of alcohol and water, preferably methanol and water is used in the liquid-liquid extraction.

In a preferred embodiment of the invention the oxygenate extraction process is a liquid-liquid extraction process that preferably takes place in an extraction column using a mixture of methanol and water as the solvent, wherein an extract from the liquid-liquid extraction is sent to a solvent recovery column from which a tops product comprising methanol, olefins and paraffins is recycled to the extraction column, thereby enhancing the overall recovery of olefins and paraffins. A bottoms product from the solvent recovery column may also be recycled to the extraction column. The solvent preferably has a water content of more than 3% by weight, more preferably a water content of about 5%-15% by weight. A raffinate from the extraction column may be sent to a stripper column from which a hydrocarbon feed stream containing more than 90% by weight olefins and paraffins and typically less than 0.2% by weight, preferably less than 0.02% by weight oxygenates exits as a bottoms product. Preferably the recovery of olefins and paraffins in the hydrocarbon feed stream is in excess of 70%, more preferably in excess of 80%, while the olefin/paraffin ratio is at least substantially preserved.

This invention specifically relates to a fractionated hydrocarbon condensate product from a low temperature Fischer-Tropsch reaction in the $C_{10}$ to $C_{13}$ range containing 10 to 30%, typically less than 25%, by weight olefins with a high degree of linearity of greater than 92%, typically greater than 95%, for use in a process for manufacturing linear alkyl benzene.

The invention also relates to a linear alkyl benzene product formed by an alkylation process of olefins, said olefins being a product of a low temperature Fischer-Tropsch reaction, wherein the linear alkyl benzene product has a linearity of greater than 90%, preferably greater than 94%.

DESCRIPTION OF PREFERRED EMBODIMENTS

Figure 1:
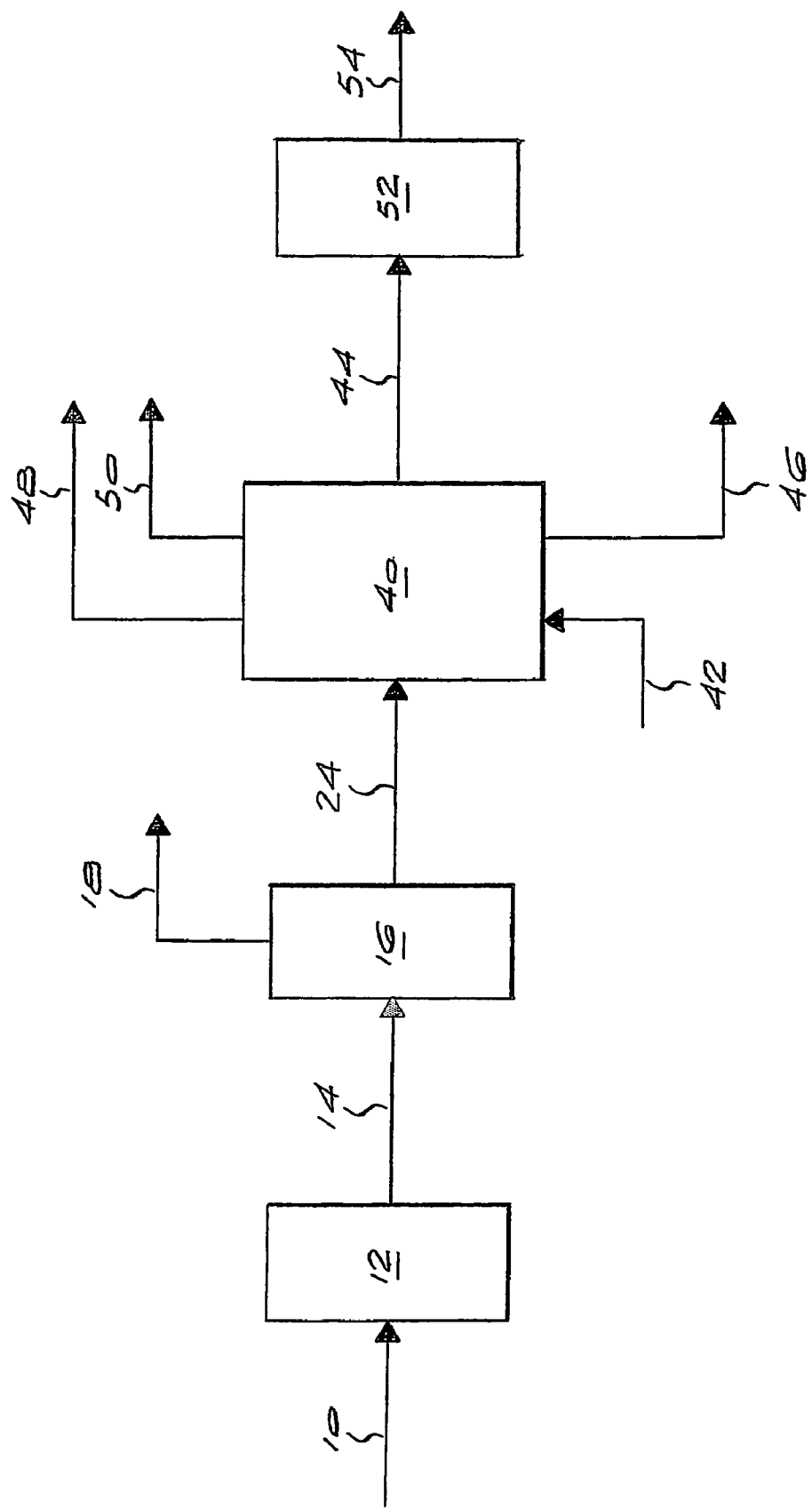
FIG. 1 is a block diagram of a process according to the invention for producing linear alkyl benzene.

This invention relates to the use of a hydrocarbon condensate stream from a low temperature Fischer-Tropsch reaction in the production of linear alkyl benzene. A linear paraffin product is also produced.

In the Fischer-Tropsch process, synthesis gas (carbon monoxide and hydrogen) obtained from gasification of coal or reforming of natural gas, is reacted over a Fischer Tropsch catalyst to produce a mixture of hydrocarbons ranging from methane to waxes and smaller amounts of oxygenates.

In a low temperature Fischer-Tropsch reaction, the reaction takes place in a slurry bed reactor or fixed bed reactor, preferably a slurry bed reactor, at a temperature in the range of 160° C.-280° C., preferably 210° C.-260° C., and a pressure in the range of 18-50 bar, preferably between 20-30 bar, in the presence of a catalyst. The catalyst may include iron, cobalt, nickel or ruthenium. However, a cobalt-based catalyst is preferred for the low temperature reaction. Usually, the cobalt catalyst is supported on an alumina support.

During the low temperature Fischer-Tropsch reaction, a lighter hydrocarbon vapour phase is separated from a liquid phase comprising heavier liquid hydrocarbon products. The heavier liquid hydrocarbon product (waxy products) is the major product of the reaction and may, for example, be hyrocracked to produce diesel and naphtha.

The lighter hydrocarbon vapour phase which comprises gaseous hydrocarbon products, unreacted synthesis gas and water is condensed to provide a "condensation product" which comprises an aqueous phase and a hydrocarbon condensation product phase.

The hydrocarbon condensation product includes olefins and paraffins in the $C_4$ to $C_{26}$ range, and oxygenates including alcohols, esters, aldehydes, ketones and, acids. This product is typically fractioned into the $C_8$ to $C_{16}$ range, preferably into the $C_{10}$ to $C_{13}$ range.

In the case of a supported cobalt based catalyst, olefins, which are predominantly alpha olefins, only make up approximately 10% to 30%, typically less than 25%, by weight, of the fractionated hydrocarbon condensation product. Generally, this product would not be considered useful in an alkylation reaction to form linear alkyl benzene, because of the presence of oxygenates that need to be removed. Oxygenate removal is required since oxygenates impair the activity of downstream catalysts. This is especially detrimental to solid acid catalysts, such as UOP's DETAL™ catalyst, since it negatively impacts catalyst lifetime, thereby necessitating more frequent catalyst replacement. However, it has been found that the olefins in the low temperature Fischer-Tropsch hydrocarbon condensate product have a very high degree of linearity of greater than 95% and, even though they only make up 10 to 30% typically less than 25%, by weight of the hydrocarbon condensate product, it is an excellent feed for the production of linear alkyl benzene and provides an economically viable manner for the production of highly linear alkyl benzene. The fractionated hydrocarbon condensation product includes 60% to 80% by weight paraffins which have a linearity of greater than 92%, and 5% to 15% by weight oxygenates.

Referring to FIG. 1, by way of example, a hydrocarbon condensate product 10 from a low temperature Fischer-Tropsch reaction using a cobalt catalyst contains 20% by weight olefins, 74% by weight paraffins, and 6% by weight oxygenates. The hydrocarbon condensate product 10 is passed through a fractionation column 12 and a $C_{10}$-$C_{13}$ cut 14 is separated therefrom. The cut 14 contains 22% by weight olefins, 71% by weight paraffins and 7% by weight oxygenates. The cut 14 is then sent to an oxygenate removal unit 16 where the oxygenates 18 are removed to provide a hydrocarbon feed stream 24 containing 23% by weight olefins and 77% by weight paraffins and less than 0.015% by weight oxygenates.

As mentioned above, the olefin concentration in the cut 14 is low. It is therefore desirable to use an oxygenate removal step which preserves the olefin concentration. In the prior art, many methods of removing oxygenates from hydrocarbon streams are suggested. Such removal methods include hydrogenation, azeotropic distillation, extractive distillation, vapour phase dehydration, liquid phase dehydration, liquid-liquid extraction. Distillation, liquid-liquid extraction and dehydration processes are preferred as they tend to preserve the olefin concentration. Typically the required recovery of olefins and paraffins in stream 24 is in excess of 70% of the olefins and paraffins in stream 14, while at least substantially preserving the olefin/paraffin ratio.

Figure 2:
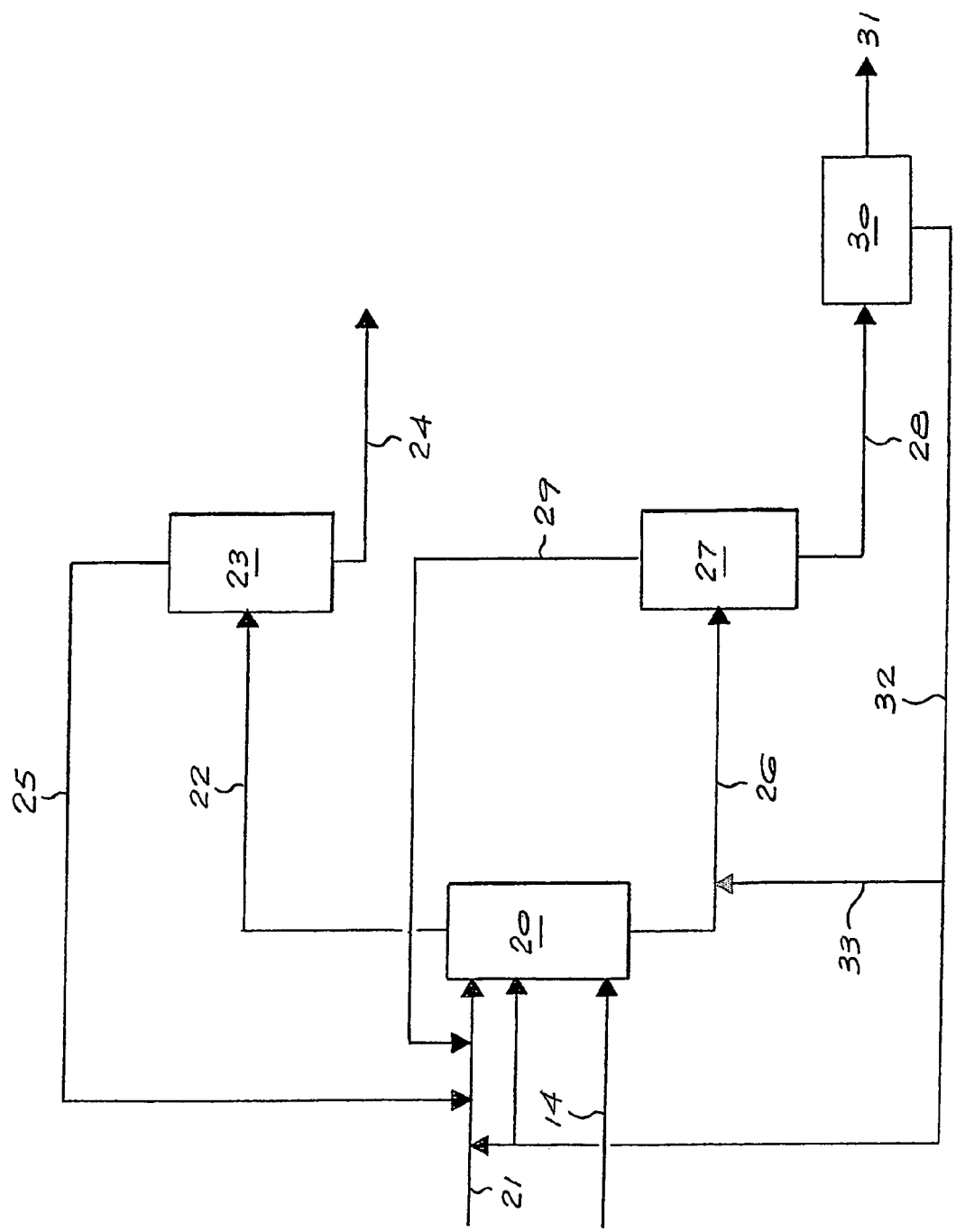
FIG. 2 is a block diagram of a process for extracting oxygenates from a hydrocarbon product, used in the process of FIG. 1.

With reference to FIG. 2, a liquid-liquid extraction process of the invention includes an extraction column 20. The fractionated condensation product of a low temperature Fischer-Tropsch reaction described above 14 is fed into the extraction column 20 at, or near, the bottom thereof and a solvent stream 21 comprising a mixture of methanol and water is fed into the extraction column 20 at or near the top thereof. The solvent stream 21 preferably comprises more than 5% by weight, typically 6% by weight, water. The solvent to feed ratio in the solvent stream is low, typically less than 1.5, usually about 1.25.

Raffinate 22 from the top of the extraction column 20, which includes olefins and paraffins and a small amount of solvent, enters a raffinate stripper column 23 and a hydrocarbon product stream comprising more than 90% by weight olefins and paraffins usually up to 99% by weight olefins and paraffins and less than 0.2% by weight, preferably less than 0.02% by weight oxygenates exits as a bottoms product 24.

The bottoms product 24, which shows an overall recovery of over 90% of the olefins and paraffins contains more than 20% by weight α-olefins and more than 70% by weight n-paraffins. Thus, the olefin content of the hydrocarbon product (which is intended for use in the production of linear alkyl benzene) has been preserved. A solvent comprising mainly methanol (more than 90% by weight) and low concentrations of water (less than 5% by weight) and olefins/paraffins (less than 5% by weight) exits as a tops product 25 and is returned to the solvent feed stream 21. If it is desired to recover the bottoms product 24 as a vapour stream, this can be done by taking a bottoms vapour stream from the column 20. The liquid product from the column 20 will then be a very small effluent stream.

An extract 26 is drawn from the bottom of the extraction column 20 and is fed to solvent recovery column 27. A tops product 29 from the solvent recovery column 27 comprises over 90% by weight methanol, and olefins and paraffins. Up to 60% of the olefins and paraffins from the extract 26 are recovered to the tops product 29. The tops product is then recycled to the solvent stream 21. The oxygenate content of the tops product 29 can be as low as 50 ppm, depending on the solvent to feed ratio used in the extraction column 20. A bottoms product 28 from the solvent recovery column 27 comprises mainly water, oxygenates and olefins/paraffins. This bottoms product 28 forms two liquid phases that can be decanted in a decanter 30. The organic phase is an oxygenate, olefin and paraffin stream 31, which leaves the process as a product. The aqueous phase is a stream 32, which is recycled to the extraction column 20. This stream 32 can either enter the extraction column at the top along with the solvent stream 21, or slightly lower down the column 20, to prevent the low amount of oxygenates that will be present in this stream from appearing in the raffinate stream 22.

Normally a high-boiling solvent is preferred for liquid-liquid extraction because the solvent recovery steps after extraction requires less energy than will be the case for a low-boiling solvent. However, it has been found that a mixture of methanol and water, which is a low-boiling solvent, need not suffer from this drawback, because it can be effective at low solvent to feed ratios (this can be lower than 1 if the required oxygenate extraction is not too severe).

A study of the different azeotropes that exist between components in the feed and water would lead one to expect that it would not be possible to distil water overhead in the solvent recovery column 27 without azeotroping oxygenates overhead as well. Surprisingly, this turns out not to be the case. Methanol, which does not form azeotropes with any of the other species present, prevents the water/oxygenate azeotropes from distilling over at the same temperature as the paraffins and olefins. This appears to be due to an extractive distillation effect. Additionally, it is possible to distil the paraffins and olefins overhead, while recovering the oxygenates as a bottoms product. This has the effect of enhancing the overall paraffin and olefin recovery of the process, because the overheads 29 of the solvent recovery column 27 is recirculated to the extraction column 20, which means that the paraffins and olefins will be forced to leave the process in the product stream 24.

It is therefore possible to have a hydrocarbon stream 24 with a high overall recovery of olefins and paraffins, without the use of a counter solvent in the extraction column. In this mode of operation, all the methanol, and part of the water (10-50%) are also recovered in the overhead stream 29.

When operating a solvent recovery column 27 in the manner described above, it is to be expected that certain species may become trapped in the column. These species will tend to build up and in the process cause unstable operation of the solvent recovery column. Such species would typically be heavier olefins and paraffins or lighter oxygenates in the present case. Operating the solvent recovery column with a small side draw may prevent the build up of such species and thereby result in much improved operability of the system.

It is also possible to run the extraction column 20 and the solvent recovery column 27 at different methanol/water ratios. This may be desirable because a high water content in the extraction column 20 will lead to increased solvent to feed ratios (because of reduced solubility of oxygenates in the solvent), while a certain amount of water is necessary to achieve the extractive distillation effect in combination with methanol to recover all the paraffins and olefins as overhead products in the solvent recovery column 27. The different methanol/water ratios in the two columns (20 and 27) can be achieved by diverting some of the water in stream 32 to stream 26 by means of a stream 33.

After passing the $C_{10}$-$C_{13}$ hydrocarbon feed stream mentioned above through the abovementioned oxygenate extraction process using a mixture of methanol (95% by weight) and water (5% by weight) and a solvent to feed ratio of 1.25, the purified hydrocarbon feed stream 24 contains 22% by weight olefins, 76% by weight paraffins and less than 0.02% by weight oxygenates. Not only does the extraction process extract oxygenates with good recovery of olefins and paraffins, it also preserves the olefin content of the hydrocarbon feed. The recovery of olefins and paraffin is 89.9%, while the ratio of olefins to paraffins is substantially preserved. The purified hydrocarbon feed stream containing olefins is particularly useful in the production of linear alkyl benzene.

The oxygenate removal process may include a final adsorption step to further reduce the oxygenate content to less than 0.015%. The further reduced oxygenate level will depend on the requirements of the chosen alkylation system and may be as low as 0.0001%.

Referring back to FIG. 1, according to the invention, the liquid hydrocarbon product 24 from the oxygenate removal process 16 is introduced into an alkylation reactor 40. The alkylation reaction may be carried out by using a Friedel-Crafts type condensation catalyst such as $AlCl_3$, $H_2SO_4$, $BF_3$, HF, preferably a solid acid catalyst. In the present case, UOP's DETAL™ solid-acid catalyst alkylation technology is used. Typically, the alkylation reaction is carried at temperatures of greater than 100° C. and pressures of about 300 kPa (abs) in the presence of UOP's proprietary DETAL™ catalyst (see Smith R. (1991) Linear alkyl benzene by heterogeneous catalysis. PEP Review No. 90-2-4, SRI International). In this process, benzene 42 and the olefin component of the liquid hydrocarbon product 24 are reacted in the alkylation reactor 40 using a solid acid catalyst to produce highly linear alkyl benzene 44 with linearity greater than 94%. The linear alkylbenzene produced by the process of the invention is comparable to commercial grade linear alkyl benzene produced in conventional processes based on kerosene feedstock. Heavy alkylates 46 and paraffins 48 are removed. The paraffins 48, which do not react in the reactor, have a linearity greater than 92% and may be sold or may be used in further process, for example they may be dehydrogenated and used in a conventional process for producing linear alkyl benzene. Benzene 50 is recovered and recycled to the alkylation reactor.

It is also possible to use reactive distillation (also known as catalytic distillation) to perform the alkylation step, where the catalyst is contained inside a distillation column, and the separation of the unreacted reagents and products occur as soon as the products are formed. In this manner the reactor and product purification functionality are partly combined into a single unit operation.

The highly linear alkyl benzene 44 is then introduced to a sulphonation reactor 52 and sulphonated using sulphuric acid, oleum or sulphur trioxide. Sulphur trioxide is currently the preferred process. The sulphonation process results in the formation of a highly linear alkyl benzene sulphonates 54.

The process of the invention makes use of a feed stream in the form of a condensation product from a low temperature Fischer-Tropsch reaction which would not, ordinarily, be thought of for producing linear alkyl benzene. The process produces a desirable highly linear alkyl benzene product with linearity above 94%, while at the same time producing a high quality paraffin product which may be sold or used in further processes, making the process economically viable. To give an example, of the total global $C_8$-$C_{16}$ paraffin demand most of the demand is for the $C_{10}$-$C_{13}$ fraction, which is used predominantly for LAB production, detergent alcohol production and miscellaneous industrial uses.

The extraction step of the invention will now be described in more detail with reference to the following non-limiting example.

EXAMPLE

This example shows a process according to the invention. The extraction column 20 was run at a solvent to feed ratio of 1.25 and a temperature of 50° C. The overall olefin/paraffin recovery in the stream 24 was 89.9%. The olefin/paraffin ratio in the feed was 1:3.7 and 1:3.6 post oxygenate extraction.

Extraction column 20

| | Stream | | | | | | | |
|---|---|---|---|---|---|---|---|---|
| | 14 | | 21 | | 22 | | 26 | |
| | Comp (wt %) | Flow (kg/hr) | Comp (wt %) | Flow (kg/hr) | Comp (wt %) | Flow (kg/hr) | Comp (wt %) | Flow (kg/hr) |
| Total | 100 | 3000 | 100 | 3750 | 100 | 2530 | 100 | 4220 |
| Total C10-C13 P/O | 92.7 | 2779.7 | 2.16 | 81.0 | 99.1 | 2507.9 | 6.20 | 261.7 |
| Total Oxygenates | 7.3 | 217.7 | 0.000 | 0.000 | 0.0144 | 0.365 | 5.78 | 243.7 |
| Lights and Heavies | 0.057 | 1.7 | 0.004 | 0.144 | 0.0104 | 0.263 | 0.00480 | 0.202 |
| Water | 0.031 | 0.934 | 6.01 | 225.6 | 0.0073 | 0.184 | 5.74 | 242.4 |
| Methanol | 0.000 | 0.000 | 91.7 | 3443.3 | 0.842 | 21.31 | 82.3 | 3472.0 |

Raffinate Stripper column 23

| | Stream | | | | | |
|---|---|---|---|---|---|---|
| | 22 | | 25 | | 24 | |
| | Comp (wt %) | Flow (kg/hr) | Comp (wt %) | Flow (kg/hr) | Comp (wt %) | Flow (kg/hr) |
| Total | 100 | 2530 | 100 | 30 | 100 | 2500 |
| Total C10-C13 P/O | 99.1 | 2507.9 | 2.63 | 0.793 | 99.97 | 2499.4 |
| Total Oxygenates | 0.0144 | 0.365 | 0.00163 | 0.000491 | 0.0145 | 0.363 |
| Lights and Heavies | 0.0104 | 0.263 | 0.0887 | 0.0267 | 0.00808 | 0.202 |
| Water | 0.0073 | 0.184 | 1.52 | 0.456 | 0.00115 | 0.0288 |
| Methanol | 0.842 | 21.31 | 95.4 | 28.7 | 0.000 | 0.000 |

Solvent Recovery column 27

| | Stream | | | | | |
|---|---|---|---|---|---|---|
| | 26 | | 29 | | 28 | |
| | Comp (wt %) | Flow (kg/hr) | Comp (wt %) | Flow (kg/hr) | Comp (wt %) | Flow (kg/hr) |
| Total | 100 | 4220 | 100 | 3584 | 100 | 636 |
| Total C10-C13 P/O | 6.20 | 261.7 | 2.37 | 85.1 | 27.6 | 175.8 |
| Total Oxygenates | 5.78 | 243.7 | 0.00140 | 0.0503 | 42.0 | 267.0 |
| Lights and Heavies | 0.00480 | 0.202 | 0.00747 | 0.268 | 0.00279 | 0.0177 |
| Water | 5.74 | 242.4 | 1.30 | 46.8 | 29.3 | 186.6 |
| Methanol | 82.3 | 3472.0 | 96.2 | 3451.9 | 1.04 | 6.63 |

The invention claimed is:

1. A process for producing linear alkyl benzene and linear paraffins, the process including the steps of obtaining a hydrocarbon condensate containing olefins, paraffins and oxygenates from a low temperature Fischer-Tropsch reaction;
   a) fractionating a desired carbon number distribution from the hydrocarbon condensate to form a fractionated hydrocarbon condensate stream which is the product of a Fischer-Tropsch reaction;
   b) extracting oxygenates from the fractionated hydrocarbon condensate stream from step a) to form a raffinate stream containing olefins and paraffins which is the product of a Fischer-Tropsch reaction;
   c) directly feeding the raffinate stream containing olefins and paraffins from step b) to an alkylating stage with benzene in the presence of a suitable alkylation catalyst to produce linear alkyl benzene and linear paraffin; and
   d) recovering linear alkyl benzene and linear paraffin.

2. The process according to claim 1, wherein, in the extraction step b), the olefin/paraffin ratio of the stream is substantially preserved.

3. The process according to claim 1, wherein the low temperature Fischer-Tropsch reaction is carried out at a temperature of 160° C.-280° C. to provide a hydrocarbon condensate containing 60 to 80% by weight paraffins and 10 to 30% by weight olefins.

4. The process according to claim 3, wherein the Fischer-Tropsch reaction is carried out at a temperature of 210° C.-260° C.

5. The process according to claim 3, wherein the Fischer-Tropsch reaction is carried out in the presence of a cobalt catalyst.

6. The process according to claim 3, wherein the hydrocarbon condensate contains less than 25% by weight olefins.

7. The process according to claim 3, wherein the olefins in the hydrocarbon condensate have a degree of linearity of greater than 95%.

8. The process according to claim 7, wherein the paraffins in the hydrocarbon condensate have a degree of linearity of greater than 92%.

9. The process according to claim 1, wherein the hydrocarbon condensate is fractionated, in step a), into the $C_8$ to $C_{16}$ range.

10. The process according to claim 9, wherein the hydrocarbon condensate product is fractionated, in step a), into the $C_{10}$ to $C_{13}$ range.

11. The process according to claim 10, wherein the fractionated hydrocarbon product contains 10 to 30% by weight olefins with a degree of linearity greater than 92%.

12. The process according to claim 1, wherein the oxygenates are extracted, in step b), by distillation, liquid-liquid extraction or dehydration.

13. The process according to claim 12, wherein the oxygenates are extracted by liquid-liquid extraction.

14. The process according to claim 13, wherein a light solvent is used in the liquid-liquid extraction.

15. The process according claim 14, wherein the light solvent is a mixture of methanol and water.

16. The process according to claim 15, wherein the oxygenate extraction process is a liquid-liquid extraction process that takes place in an extraction column using a mixture of methanol and water as the solvent, wherein an extract from the liquid-liquid extraction is sent to a solvent recovery column from which a tops product comprising methanol, olefins and paraffins is recycled to the extraction column, thereby enhancing the overall recovery of olefins and paraffins.

17. The process according to claim 16, wherein a bottoms product from the solvent recovery column is recycled to the extraction column.

18. The process according to claim 16, wherein a raffinate from the extraction column is sent to a stripper column from which a hydrocarbon stream containing more than 90% by weight olefins and paraffins and less than 0.2% by weight oxygenates exits as a bottoms product.

19. The process according to claim 18, wherein the bottoms product contains less than 0.02% by weight oxygenates.

20. The process according to claim 15, wherein the solvent has a water content of more than 3% by weight.

21. The process according to claim 20, wherein the solvent has a water content of from 5%-15% by weight.

22. The process according to claim 1, wherein the recovery of olefins and paraffins in the hydrocarbon feed stream over the extraction step b) is in excess of 70%.

23. The process according to claim 22, wherein the recovery of olefins and paraffins is in excess of 80%.

24. The process according to claim 1, wherein the olefin/paraffin ratio of the fractionated hydrocarbon condensate stream a) is substantially preserved over the extraction step b).

25. The process according to claim 1, wherein the alkylation catalyst in step c) is a solid acid catalyst.

* * * * *